(12) United States Patent
Kim et al.

(10) Patent No.: US 12,064,498 B2
(45) Date of Patent: Aug. 20, 2024

(54) FOAM TYPE SEMI-PERMANENT HAIR DYEING COMPOSITION

(71) Applicant: KOLMAR KOREA CO., LTD., Sejong (KR)

(72) Inventors: Dong Min Kim, Gwangmyeong-si (KR); In Ki Hong, Sejong (KR)

(73) Assignee: KOLMAR KOREA CO., LTD., Sejong (KR)

( * ) Notice: Subject to any disclaimer, the term of this patent is extended or adjusted under 35 U.S.C. 154(b) by 88 days.

(21) Appl. No.: 17/802,874

(22) PCT Filed: Feb. 1, 2021

(86) PCT No.: PCT/KR2021/001298
§ 371 (c)(1),
(2) Date: Aug. 26, 2022

(87) PCT Pub. No.: WO2021/215629
PCT Pub. Date: Oct. 28, 2021

(65) Prior Publication Data
US 2023/0099346 A1    Mar. 30, 2023

(30) Foreign Application Priority Data

Apr. 20, 2020    (KR) .................. 10-2020-0047223

(51) Int. Cl.
| | | |
|---|---|---|
| *A61Q 5/10* | (2006.01) | |
| *A61K 8/04* | (2006.01) | |
| *A61K 8/34* | (2006.01) | |
| *A61K 8/41* | (2006.01) | |
| *A61Q 5/06* | (2006.01) | |

(52) U.S. Cl.
CPC .............. *A61K 8/046* (2013.01); *A61K 8/345* (2013.01); *A61K 8/416* (2013.01); *A61Q 5/065* (2013.01); *A61Q 5/10* (2013.01); *A61K 2800/43* (2013.01)

(58) Field of Classification Search
CPC ........ A61K 8/046; A61K 8/345; A61K 8/416; A61K 2800/43; A61K 8/34; A61K 8/604; A61K 8/86; A61K 8/41; A61K 2800/222; A61K 2800/596; A61Q 5/065; A61Q 5/10
USPC .............................................................. 8/405
See application file for complete search history.

(56) References Cited

U.S. PATENT DOCUMENTS

| | | | | |
|---|---|---|---|---|
| 4,690,685 A | * | 9/1987 | Grollier | .............. C09B 67/0033 |
| | | | | 8/408 |
| 5,735,910 A | * | 4/1998 | Lagrange | .............. C07C 323/41 |
| | | | | 8/405 |

FOREIGN PATENT DOCUMENTS

| | | | | |
|---|---|---|---|---|
| EP | 3501488 A1 | * | 6/2019 | ............... A61Q 5/02 |
| JP | 2004-269400 A | | 9/2004 | |
| JP | 2012-097026 A | | 5/2012 | |
| JP | 2012-162466 A | | 8/2012 | |

(Continued)

*Primary Examiner* — Eisa B Elhilo
(74) *Attorney, Agent, or Firm* — Bridgeway IP Law Group, PLLC; Sang Ho Lee; Hyun Woo Shin

(57) ABSTRACT

Provided is a semi-permanent hair dye composition, and particularly, a foam-type semi-permanent hair dye composition which is easily applied onto the inner part of the hair due to having high foam forming ability and high foam retention and exhibits less color fading after dyeing and excellent colorability. The semi-permanent hair dye composition includes a pigment penetration agent, a cationic surfactant, and a non-ionic surfactant as well as a basic pigment.

11 Claims, 1 Drawing Sheet
(1 of 1 Drawing Sheet(s) Filed in Color)

(56) References Cited

FOREIGN PATENT DOCUMENTS

| | | | |
|---|---|---|---|
| JP | 2012162466 A * | 8/2012 | ............... A61Q 5/10 |
| JP | 2017-095373 A | 6/2017 | |
| JP | 2020-033495 A | 3/2020 | |
| KR | 10-2016-0117200 A | 10/2016 | |
| KR | 10-2020-0026087 A | 3/2020 | |
| TW | 201249466 A1 | 12/2012 | |
| WO | WO 2017117522 A1 * | 7/2017 | ............... A61Q 5/00 |

\* cited by examiner (a)

(b)

(a)

(b)

FOAM TYPE SEMI-PERMANENT HAIR DYEING COMPOSITION

TECHNICAL FIELD

The present invention relates to a foam-type semi-permanent hair dye composition, and particularly, to a foam-type semi-permanent hair dye composition which is easily applied onto the inner part of the hair due to having high foam forming ability and high foam retention and exhibits less color fading after dyeing and excellent colorability by including a pigment penetration agent, a cationic surfactant, and a non-ionic surfactant as well as a basic pigment.

BACKGROUND ART

Consumers' interest in products that allow their personality to be expressed by dyeing their hair with various colors has been continuous. Hair dyes for dyeing hair are divided into permanent hair dyes, semi-permanent hair dyes, and temporary hair dyes according to the degree of penetration into the hair and duration of the dye.

Permanent hair dyes enable the implementation of a desired color with only one application of the dye and have good durability, but there is a problem in that they cause severe damage to the hair and contain irritating substances that may cause allergies. On the other hand, semi-permanent hair dyes have poor color durability, but there are advantages in that they are less irritative to the hair, are less likely to cause allergies, are easy to use, and develop a color in a short time. Therefore, as the importance of semi-permanent hair dyes continues to increase in busy modern society, there is a growing demand therefor.

However, unlike permanent hair dyes that penetrate into the hair, semi-permanent hair dyes, which are to be attached to the hair surface by an ionic bond, have disadvantages in that durability is poor due to a weak dye uptake effect and the dye is allowed to contact the hair for a long period of time or needs to be repeatedly used several times to obtain a desired dye uptake effect. When the content of a pigment increases to enhance a dyeing effect, skin discoloration occurs, and when the content of a pigment penetration agent such as benzyl alcohol or the like increases to enhance pigment penetrability, the conditioning of hair is degraded. When the content of a cationic surfactant increases to enhance the conditioning of hair increases, dyeing efficiency is degraded.

Meanwhile, semi-permanent hair dyes may be prepared in various formulations such as creams, powders, liquids, bubbles, aerosols, and the like. Among them, the cream type, which is widely sold in the market, has a disadvantage in that application thereof onto the inner part of the hair is difficult because it is generally applied to the hair using a brush due to the characteristics of the formulation. For this reason, the hair is not uniformly dyed and thus becomes stained.

Therefore, the development of a semi-permanent hair dye composition, which is excellent in color development and durability and is easily applied onto the inner part of the hair, is required.

DISCLOSURE

Technical Problem

The present invention is directed to providing a foam-type semi-permanent hair dye composition which is easily applied onto the inner part of the hair due to having high foam forming ability and high foam retention and exhibits less color fading after dyeing and excellent colorability by including a cationic surfactant and a non-ionic surfactant as well as a basic pigment.

However, the technical objectives of the present invention are not limited to that described above, and other unmentioned technical objectives will be clearly understood by those skilled in the art from the following description.

Technical Solution

One aspect of the present invention provides a composition for a semi-permanent hair dye, which includes a basic pigment, a pigment penetration agent, and a surfactant consisting of a cationic surfactant and a non-ionic surfactant.

Preferably, the pigment penetration agent includes at least one of benzyl alcohol and dipropylene glycol.

In addition, preferably, the cationic surfactant includes one or more selected from the group consisting of cetrimonium chloride, steartrimonium chloride, steartrimonium chloride/propylene glycol, behentrimonium chloride, behentrimonium methosulfate, steartrimonium, cocamidopropyl dimethylamine, stearamidopropyl dimethylamine, behenamidopropyl dimethylamine, palmitamidopropyltrimonium chloride, dipalmitoylethyl hydroxyethylmonium methosulfate, and mixtures thereof.

In addition, preferably, the non-ionic surfactant includes one or more selected from the group consisting of decyl glucoside, C12-14 pareth-12, coco glucoside, lauryl glucoside, laureth-4, laureth-12, octyl glucoside, nonyl glucoside, octyl maltoside, octyl thioglucoside, coconut oil alkyl glucoside, and mixtures thereof.

In addition, preferably, a content ratio of the pigment penetration agent and the surfactant is 1:1.5 to 9.5.

In addition, preferably, a content ratio of the cationic surfactant and the non-ionic surfactant is 1:1.5 to 5.5.

In addition, preferably, the non-ionic surfactant is included in a larger amount than the cationic surfactant.

In addition, preferably, the benzyl alcohol is included in an amount of 0.1 to 2.0 wt % based on the total weight of the composition, and the dipropylene glycol is included in an amount of 0.1 to 10 wt % based on the total weight of the composition.

In addition, preferably, the cationic surfactant is included in an amount of 0.5 to 20 wt % based on the total weight of the composition.

In addition, preferably, the non-ionic surfactant is included in an amount of 1 to 30 wt % based on the total weight of the composition.

In addition, preferably, the composition is a liquid formulation.

In addition, preferably, the composition is a foam type capable of forming bubbles.

Advantageous Effects

A semi-permanent hair dye composition according to the present invention has good dyeing efficiency due to exhibiting less color fading after dyeing and excellent colorability.

In addition, since a cationic surfactant and a non-ionic surfactant are used together, foam forming ability and foam retention are high, and thus a formulation does not drip when applied onto the hair and is easily applied onto the inner part of the hair.

Additionally, uniform hair dyeing is possible, the uptake of the dye to the skin during dyeing can be minimized, and a conditioning effect can be provided to the hair.

DESCRIPTION OF DRAWINGS

The patent or application file contains at least one drawing executed in color. Copies of this patent or patent application publication with color drawing(s) will be provided by the Office upon request and payment of the necessary fee.

In order to more fully understand the drawings mentioned in the detailed description of the present invention, a brief description of each drawing is provided.

MODES OF THE INVENTION

Figure 1:
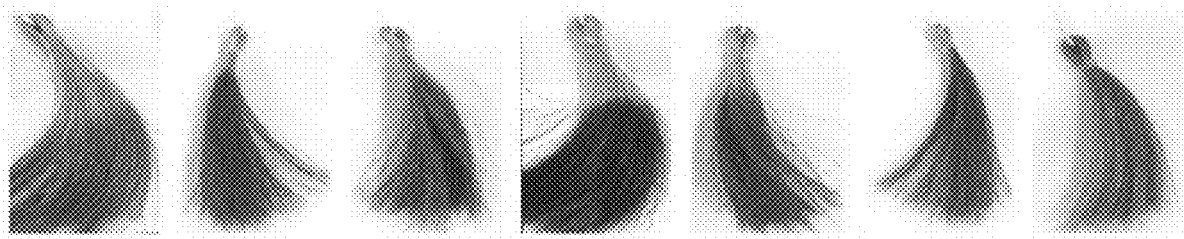
FIG. 1 show images for observing the colorability of examples (a) and comparative examples (b) prepared according to components shown in Table 1.
Figure 1:
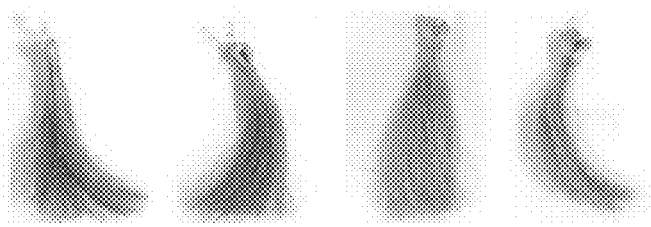

Unless otherwise defined, all technical and scientific terms used herein have the same meaning as commonly understood by those skilled in the art. In general, the nomenclature used herein is well known and commonly used in the art. Further, in the description of embodiments of the present invention, a detailed description of known functions and configurations incorporated herein will be omitted to avoid making the subject matter of the present invention unclear. Further, although embodiments of the present invention are described below, the present invention may be embodied in many alternate forms by those skilled in the art without departing from the spirit of the present invention and should not be construed as limited to only the embodiments set forth herein.

The present invention relates to a semi-permanent hair dye composition, and particularly, to a foam-type semi-permanent hair dye composition excellent in foam forming ability and foam retention by including a pigment penetration agent, a cationic surfactant, and a non-ionic surfactant as well as a basic pigment. The foam-type semi-permanent hair dye composition according to the present invention may include a basic pigment, a pigment penetration agent, a cationic surfactant, and a non-ionic surfactant.

Hereinafter, components of the semi-permanent hair dye composition according to the present invention will be described in detail.

In the composition according to the present invention, the basic pigment is intended to provide a coloring effect to the hair and refers to a dye whose ion is a cation. Since the basic pigment has a positive charge, it is adsorbed to the hair having a negative charge by electrostatic attraction.

The basic pigment of the present invention is not particularly limited and may be, for example, BASIC BLUE 3, BASIC BLUE 6, BASIC BLUE 7, BASIC BLUE 9, BASIC BLUE 26, BASIC BLUE 41, BASIC BLUE 47, BASIC BLUE 99, BASIC BROWN 4, BASIC BROWN 16, BASIC BROWN 17, BASIC GREEN 1, BASIC GREEN 4, BASIC ORANGE 1, BASIC ORANGE 2, BASIC ORANGE 31, BASIC RED 1, BASIC RED 1:1, BASIC RED 2, BASIC RED 22, BASIC RED 46, BASIC RED 51, BASIC RED 76, BASIC RED 118, BASIC VIOLET 1, BASIC VIOLET 2, BASIC VIOLET 3, BASIC VIOLET 4, BASIC VIOLET 10, BASIC VIOLET 11:1, BASIC VIOLET 14, BASIC VIOLET 16, BASIC YELLOW 11, BASIC YELLOW 28, BASIC YELLOW 40, BASIC YELLOW 57, or BASIC YELLOW 87. The basic pigment of the present invention may be selected according to a desired color.

In the present invention, the basic pigment may be included in an amount of 0.001 to 1.5 wt % based on the total weight of the composition, and the weight thereof may be adjusted according to a color. When the content of the basic pigment is less than 0.001 wt % based on the total weight of the composition, color development is degraded, and when the content of the basic pigment exceeds 1.5 wt %, the skin is dyed.

In the composition according to the present invention, the pigment penetration agent is intended to enhance the penetrability of a pigment and serves to allow a pigment to penetrate into the hair cuticle.

The pigment penetration agent of the present invention may be included in an amount of 0.1 to 12 wt %, preferably 4 to 9 wt %, and more preferably 5 to 7 wt %, based on the total weight of the composition. When the content of the pigment penetration agent is less than 0.1 wt %, colorability is degraded, and when the content of the pigment penetration agent exceeds 12 wt %, the conditioning of hair is degraded due to severe damage.

The pigment penetration agent of the present invention may include at least one of benzyl alcohol and dipropylene glycol. As one example, dipropylene glycol may also be used as a pigment penetration aid while using benzyl alcohol as the pigment penetration agent. When both benzyl alcohol and dipropylene glycol are used as the pigment penetration agents, color development for the hair may be enhanced.

In the present invention, benzyl alcohol may be included in an amount of 0.1 to 2.0 wt %, preferably 0.1 to 1.0 wt %, and most preferably 0.5 to 0.8 wt %, based on the total weight of the composition.

In the present invention, dipropylene glycol may be included in an amount of 0.1 to 10 wt %, preferably 4 to 8 wt %, and most preferably 5 to 6 wt %, based on the total weight of the composition.

The surfactant of the present invention includes a cationic surfactant and a non-ionic surfactant. The composition of the present invention not only provides a conditioning effect to the hair but also ensures foam forming ability and foam retention by including both a cationic surfactant and a non-ionic surfactant as the surfactants, and thus a foam-type formulation that does not drip down the hair may be implemented.

The surfactant of the present invention may be included in an amount of 1.5 to 50 wt %, preferably 5 to 40 wt %, and more preferably 10 to 35 wt %, based on the total weight of the composition. When the content of the surfactant is less than 1.5 wt %, the stability of a formulation is degraded, and when the content of the surfactant exceeds 50 wt %, dyeing efficiency is degraded.

In the composition according to the present invention, the cationic surfactant is intended to impart a conditioning effect to the hair and may include one or more selected from the group consisting of cetrimonium chloride, steartrimonium chloride, steartrimonium chloride/propylene glycol, behentrimonium chloride, behentrimonium methosulfate, steartrimonium, cocamidopropyl dimethylamine, stearamidopropyl dimethylamine, behenamidopropyl dimethylamine, palmitamidopropyltrimonium chloride, dipalmitoylethyl hydroxyethylmonium methosulfate, and mixtures thereof.

In the present invention, the cationic surfactant may be included in an amount of 0.5 to 20 wt %, preferably 1 to 15 wt %, more preferably 2 to 11, and most preferably 3 to 8 wt %, based on the total weight of the composition. When the content of the cationic surfactant is less than 0.5 wt %, a hair conditioning effect is degraded, and when the content of the cationic surfactant exceeds 20 wt %, dyeing efficiency is degraded.

In the present invention, since a mixture of the cationic surfactant and the non-ionic surfactant is used as the surfactant, a formulation that is able to form and retain bubbles may be implemented.

The non-ionic surfactant of the present invention may include one or more selected from the group consisting of decyl glucoside, C12-14 pareth-12, coco glucoside, lauryl glucoside, laureth-4, laureth-12, octyl glucoside, nonyl glucoside, octyl maltoside, octyl thioglucoside, coconut oil alkyl glucoside, and mixtures thereof.

In the present invention, the non-ionic surfactant may be included in an amount of 1 to 30 wt %, preferably 4 to 22 wt %, and most preferably 5 to 20 wt %, based on the total weight of the composition. When the content of the non-ionic surfactant is less than 1 wt %, foam retention is degraded, and when the content of the non-ionic surfactant exceeds 30 wt %, stickiness is caused.

In the present invention, the non-ionic surfactant is preferably included in a larger amount than the cationic surfactant. When a cationic surfactant and an excessive amount of a non-ionic surfactant are mixed as the surfactant, a foam-type formulation excellent in foamability and foam retention may be implemented.

In the composition according to the present invention, the content ratio of the cationic surfactant and the non-ionic surfactant may be 1:1.5 to 5.5, preferably 1:2.5 to 4.5, and most preferably 1:3. When the cationic surfactant and the non-ionic surfactant are included in the above ratio, a foam-type formulation can be stably maintained. When the content ratio of the cationic surfactant and the non-ionic surfactant is 1:less than 1.5, foam retention is degraded, and when the content ratio of the cationic surfactant and the non-ionic surfactant is 1:more than 5.5, stickiness is caused.

In addition, in the composition according to the present invention, the content ratio of the pigment penetration agent and the surfactant may be 1:1.5 to 9.5, preferably 1:3 to 8, and most preferably 1:5 to 6. When the pigment penetration agent and the surfactant are included in the above ratio, excellent colorability and formulation stability can be achieved. When the content ratio of the pigment penetration agent and the surfactant is 1:less than 1.5 or 1:more than 9.5, colorability is degraded, severe color fading occurs, and a formulation becomes unstable.

The semi-permanent hair dye composition according to the present invention may further include one or more selected from among other components (e.g., an anti-discoloration agent, a chelating agent, a pH adjusting agent, a foaming control agent, a thickening agent, a moisturizing agent, a preservative, a fragrance, and other additives) which are typically used in the art within the range not impairing the effects of the present invention.

For example, the composition according to the present invention may include polyquaternium-39, polyquaternium-10, polyquaternium-22, polyquaternium-48, or the like as the anti-discoloration agent, glycerin, methylpropanediol, butylene glycol, or the like as the foaming control agent, and sodium benzoate, 1,2-hexanediol, ethylhexylglycerin, or the like as the preservative. In addition, disodium EDTA as the chelating agent and citric acid as the pH adjusting agent may be included. However, the present invention is not limited thereto, and various functional additives typically used in the art and components included in a typical cosmetic composition may be further included.

The semi-permanent hair dye composition according to the present invention may be a liquid formulation. Unlike a conventional cream-type hair dye which is not easily applied onto the inner part of the hair, the liquid formulation is able to be applied onto the inner part of the hair. Also, the semi-permanent hair dye composition according to the present invention may be implemented in a foam-type formulation that is capable of forming bubbles. When the hair dye composition according to the present invention is applied and then rubbed, bubbles are formed, and uniform hair dyeing is possible while stably retaining the bubbles.

As described above, the present invention can implement a foam-type semi-permanent hair dye composition by including a pigment penetration agent, a cationic surfactant, and a non-ionic surfactant as well as a basic pigment. Since the semi-permanent hair dye composition according to the present invention is excellent in foam forming ability and foam retention, a formulation does not drip down the hair, and thus it is possible to uniformly dye even the inner part of the hair.

Hereinafter, examples for describing the present invention in more detail are shown as follows, but the present invention is not limited thereto.

PREPARATION EXAMPLE: PREPARATION OF EXAMPLES AND COMPARATIVE EXAMPLES

Semi-permanent hair dye compositions were prepared using components shown in Table 1 below.

Purified water, a chelating agent, glycerin, and dipropylene glycol were mixed in a beaker and dissolved by heating at 80° C. A cationic pigment was added after being separately dissolved in purified water.

Also, a cationic surfactant and a non-ionic surfactant were added after being mixed in a composition ratio shown in Table 1 below and then dissolved by heating at 80° C. The resultant was cooled to 40° C., benzyl alcohol and a preservative were added, and a fragrance was added. The resultant was stirred well and cooled to room temperature, thereby preparing semi-permanent hair dye compositions according to Examples and Comparative Examples.

Examples 1 and 2 are semi-permanent hair dye compositions in which the content of a surfactant varies, Examples 3 to 7 are semi-permanent hair dye compositions in which the ratio of a cationic surfactant and a non-ionic surfactant in a surfactant varies, Comparative Examples 1 and 2 are semi-permanent hair dye compositions in which one type of a pigment penetration agent is used, and Comparative Examples 3 and 4 are semi-permanent hair dye compositions in which the ratio of a pigment penetration agent and a surfactant varies.

TABLE 1

| Role | Component | Example 1 | Example 2 | Example 3 | Example 4 | Example 5 | Example 6 | Example 7 | Comparative Example 1 | Comparative Example 2 | Comparative Example 3 | Comparative Example 4 |
|---|---|---|---|---|---|---|---|---|---|---|---|---|
| Purification | Purified water | balance | balance | balance | balance | balance | balance | balance | balance | balance | balance | balance |
| Pigment penetration agent | Benzyl alcohol | 5.5 | 5.5 | 5.5 | 5.5 | 5.5 | 5.5 | 5.5 | 5.5 | — | 5.5 | 5.5 |
| | Dipropylene glycol | | | | | | | | — | 5.5 | | |

TABLE 1-continued

| Role | Component | | Example 1 | Example 2 | Example 3 | Example 4 | Example 5 | Example 6 | Example 7 | Comparative Example 1 | Comparative Example 2 | Comparative Example 3 | Comparative Example 4 |
|---|---|---|---|---|---|---|---|---|---|---|---|---|---|
| Surfactant | Cationic surfactant | Cetrimonium chloride/ steartrimonium chloride | 3.68 | 7.31 | 11 | 8.25 | 6.6 | 16.5 | 4.73 | 11 | 11 | 1.82 | 18.3 |
| | Non-ionic surfactant | Decyl glucoside, C12-14 pareth-12 | 7.32 | 14.69 | 22 | 24.7 | 26.4 | 16.5 | 28.27 | 22 | 22 | 3.68 | 36.66 |
| | Total | | 11 | 22 | 33 | 33 | 33 | 33 | 33 | 33 | 33 | 5.5 | 55 |
| Basic pigment | BASIC RED 51 | | | | | | | 0.5 | | | | | |
| Anti-discoloration agent | Polyquaternium-39 | | | | | | | 0.07 | | | | | |
| Chelating agent | Disodium EDTA | | | | | | | 0.1 | | | | | |
| pH adjusting agent | Citric acid | | | | | | | 0.05 | | | | | |
| Foaming control agent | Glycerin | | | | | | | 6 | | | | | |
| Preservative | Sodium benzoate | | | | | | | 0.3 | | | | | |
| Fragrance | Fragrance | | | | | | | 0.1 | | | | | |

Experimental Example 1: Evaluation of Foam Retention

Foam retention was evaluated by measuring the degree of dripping of the compositions according to Examples and Comparative Examples, and results thereof are shown in Table 2. According to an evaluation method, the hair dye compositions according to Examples and Comparative Examples were dispensed in a bubble form to 20 panelists composed of women in their 20s and 30s and applied onto their hair, and then the degree to which the shape of foam was retained without disappearing or dripping for a color development time (10 to 15 minutes) was evaluated according to the following evaluation criteria.

TABLE 2

| Classification | Foam retention | Classification | Foam retention |
|---|---|---|---|
| Example 1 | fair | Comparative Example 1 | poor |
| Example 2 | fair | Comparative Example 2 | poor |
| Example 3 | fair | Comparative Example 3 | poor |
| Example 4 | good | Comparative Example 4 | poor |
| Example 5 | fair | | |
| Example 6 | fair | | |
| Example 7 | fair | | |

<Evaluation Criteria>

Good: no dripping, Fair: slight dripping, Poor: severe dripping

As shown in Table 2, it can be confirmed that most of the compositions of Examples 1 to 7 exhibited fair or higher levels of foam retention, and thus foam retention was stable without a formulation dripping down the hair, whereas the compositions of Comparative Examples exhibited degraded foam retention with severe dripping of bubbles. From there results, it can be seen that, when a cationic surfactant and a non-ionic surfactant are mixed in a specific ratio, foam retention is high.

Experimental Example 2: Evaluation of Colorability

In order to confirm the degree of color development of the hair dye compositions of Examples and Comparative Examples for hair, colorability was evaluated.

An evaluation process was as follows. A bundle of premature gray hair containing about 30% white hair was prepared. The same amount of the prepared composition as the weight of the bundle was uniformly applied onto the bundle of premature gray hair for 5 minutes, and the bundle was washed with lukewarm water for 5 minutes and then dried by hot air using a hair dryer. This process was repeated 5 times. The repeatedly dyed bundle of premature gray hair was visually observed, and colorability was evaluated as good, fair, and poor according to the degree of coloration. Results thereof are shown in the following Table 3 and FIG. 1.

TABLE 3

| Classification | Colorability | Classification | Colorability |
|---|---|---|---|
| Example 1 | fair | Comparative Example 1 | poor |
| Example 2 | fair | Comparative Example 2 | poor |
| Example 3 | fair | Comparative Example 3 | poor |
| Example 4 | good | Comparative Example 4 | poor |
| Example 5 | fair | | |
| Example 6 | fair | | |
| Example 7 | fair | | |

As shown in Table 3 and FIG. 1, it can be confirmed that the compositions of Examples 1 to 7 exhibited fair or higher levels of colorability, and thus color development was excellent, whereas the compositions of Comparative Examples exhibited highly degraded colorability. It can be seen that, as compared to Comparative Examples 1 and 2 in which only one of benzyl alcohol and dipropylene glycol is used as a pigment penetration agent, the compositions of Examples in which both of them are used exhibit remarkably excellent colorability.

Experimental Example 3: Evaluation of Degree of Color Fading

The hair dyed in Experimental Example 2 was immersed in a shampoo liquid, subjected to shaking for 30 minutes, washed with running water for a minute, and then dried by hot air using a hair dryer. This process was repeated 5 times, and then the degree of color fading was measured. Results thereof are shown in the following Table 4 and FIG. 2.

TABLE 4

| Classification | Degree of color fading | Classification | Degree of color fading |
| --- | --- | --- | --- |
| Example 1 | slight | Comparative Example 1 | severe |
| Example 2 | slight | Comparative Example 2 | severe |
| Example 3 | almost none | Comparative Example 3 | severe |
| Example 4 | almost none | Comparative Example 4 | severe |
| Example 5 | almost none | | |
| Example 6 | slight | | |
| Example 7 | slight | | |

Figure 2:
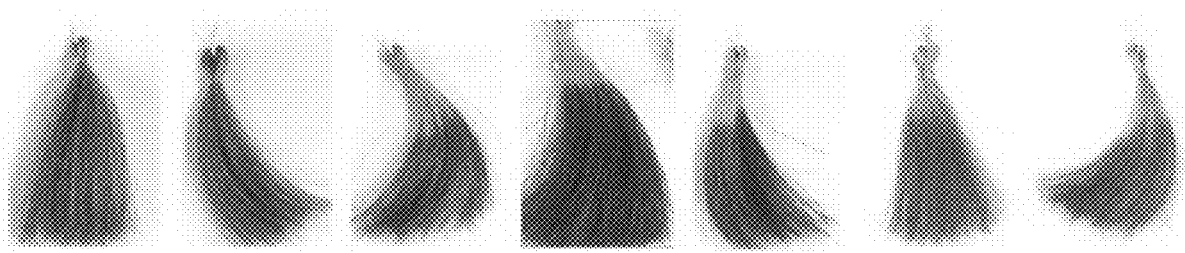
FIG. 2 show images for observing the degree of color fading of examples (a) and comparative examples (b) prepared according to components shown in Table 1.
Figure 2:
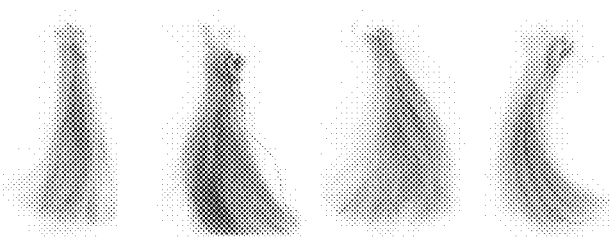

As shown in Table 4 and FIG. 2, it can be confirmed that the compositions of Examples 1 to 7 exhibited slight or almost no color fading, and thus color durability was excellent, whereas the compositions of Comparative Examples exhibited very severe color fading, and thus color durability was highly degraded. In particular, Comparative Example 1 not including benzyl alcohol exhibited severe color fading. It can be seen that, as compared to Comparative Examples 1 and 2 in which only one of benzyl alcohol and dipropylene glycol is used as a pigment penetration agent or Comparative Example 3 and 4 in which the ratio of a pigment penetration agent and a surfactant is out of a specific ratio, cases where two types of pigment penetration agents are used and the ratio of a pigment penetration agent and a surfactant falls within a specific range exhibit remarkably excellent color durability.

Experimental Example 4: Evaluation of Degree of Stickiness

The degree of stickiness when the dyed hair was washed with lukewarm water was evaluated, and results thereof are shown in Table 5. According to an evaluation method, the hair dye compositions according to Examples and Comparative Examples were applied onto the hair of 20 panelists composed of women in their 20s and 30s, and the degree of stickiness when the hair was washed with running water was evaluated.

TABLE 5

| Classification | Degree of stickiness |
| --- | --- |
| Example 1 | not sticky |
| Example 2 | not sticky |

TABLE 5-continued

| Classification | Degree of stickiness |
| --- | --- |
| Example 3 | not sticky |
| Example 4 | not sticky |
| Example 5 | slightly sticky |
| Example 6 | not sticky |
| Example 7 | slightly sticky |

As shown in Table 5, it can be confirmed that the compositions of Examples 1 to 7 were slightly sticky or had almost no stickiness. In particular, it can be confirmed that Examples 5 and 7 in which the ratio of a cationic surfactant and a non-ionic surfactant was above a specific ratio exhibited slight stickiness as compared to other Examples.

Experimental Example 5: Evaluation of Long-Term Stability

In order to evaluate the formulation stability of the hair dye compositions according to Examples and Comparative Examples, each composition was placed in a transparent container and allowed to stand under temperature conditions of 25° C., 40° C., 50° C., 5° C., and CYC (−5° C. to 40° C.) for a month, and then separation and the like according to a temperature condition were evaluated by visual observation. Results thereof are shown in the following Table 6.

TABLE 6

| Classification | Long-term formulation stability | Classification | Long-term formulation stability |
| --- | --- | --- | --- |
| Example 1 | stable | Comparative Example 1 | unstable |
| Example 2 | stable | Comparative Example 2 | unstable |
| Example 3 | stable | Comparative Example 3 | unstable due to fragrance separation and pigment precipitation |
| Example 4 | stable | Comparative Example 4 | unstable |
| Example 5 | stable | | |
| Example 6 | stable | | |
| Example 7 | stable | | |

As a result, in the case of the compositions of Examples 1 to 7, it can be confirmed that the formulation was very stably maintained for a long period of time. On the other hand, in the case of Comparative Examples 1 and 2 in which only one type of a pigment penetration agent was used, the formulation was not stably maintained for a long period of time, and in the case of Comparative Example 3 in which the ratio of a pigment penetration agent and a surfactant was lower than that of Examples, fragrance separation and pigment precipitation occurred, and thus the formulation was very unstable. In the case of Comparative Example 4 in which the ratio of a pigment penetration agent and a surfactant was higher than that of Examples, it can also be confirmed that the formulation was not stably maintained for a long period of time.

Taken together, since Examples 1 to 7 has an appropriate ratio of a surfactant to a pigment penetration agent, colorability was good, and color fading hardly occurred. Also, bubbles were stably retained after the formation of the bubbles, stickiness was hardly exhibited during washing, and the formulation was stably maintained for a long period of time.

On the other hand, in the case of Comparative Example 1 not using "dipropylene glycol" as a pigment penetration agent, poor colorability and severe color fading were exhibited, and the formulation was not stably maintained. In the case of Comparative Example 2 not using "benzyl alcohol" as a pigment penetration agent, poor colorability, severe color fading, and stickiness were exhibited. In the case of Comparative Example 3 in which the ratio of a pigment penetration agent and a surfactant was lower than that of Examples and Comparative Example 4 in which the ratio of a pigment penetration agent and a surfactant was higher than that of Examples, poor colorability and severe color fading were exhibited, and the formulations were not stably maintained.

Although a specific part of the content of the present invention has been described in detail, it will be obvious to those skilled in the art that this specific description is only a preferred embodiment and the scope of the present invention is not limited thereby. Therefore, the substantial scope of the present invention will be defined by the appended claims and their equivalents.

The invention claimed is:

1. A composition for a semi-permanent hair dye, the composition comprising:
   a basic pigment;
   a pigment penetration agent comprising benzyl alcohol and dipropylene glycol; and
   a surfactant comprising a cationic surfactant and a non-ionic surfactant,
      wherein the pigment penetration agent and the surfactant have a ratio of 1:2 to 1:9.5 by wt %.

2. The composition of claim 1, wherein the cationic surfactant comprises one or more selected from the group consisting of cetrimonium chloride, steartrimonium chloride, steartrimonium chloride/propylene glycol, behentrimonium chloride, behentrimonium methosulfate, steartrimonium, cocamidopropyl dimethylamine, stearamidopropyl dimethylamine, behenamidopropyl dimethylamine, palmitamidopropyltrimonium chloride, dipalmitoylethyl hydroxyethylmonium methosulfate, and mixtures thereof.

3. The composition of claim 1, wherein the non-ionic surfactant comprises one or more selected from the group consisting of decyl glucoside, C12-14 pareth-12, coco glucoside, lauryl glucoside, laureth-4, laureth-12, octyl glucoside, nonyl glucoside, octyl maltoside, octyl thioglucoside, coconut oil alkyl glucoside, and mixtures thereof.

4. The composition of claim 1, wherein a content weight ratio of the cationic surfactant and the non-ionic surfactant is 1:1.5 to 5.5.

5. The composition of claim 1, wherein the non-ionic surfactant is included in the composition in a larger amount than the cationic surfactant.

6. The composition of claim 1, wherein the benzyl alcohol is included in an amount of 0.1 to 2.0 wt % based on the total weight of the composition, and the dipropylene glycol is included in an amount of 0.1 to 10 wt % based on the total weight of the composition.

7. The composition of claim 1, wherein the cationic surfactant is included in an amount of 0.5 to 20 wt % based on the total weight of the composition.

8. The composition of claim 1, wherein the non-ionic surfactant is included in an amount of 1 to 30 wt % based on the total weight of the composition.

9. The composition of claim 1, wherein the composition is a liquid formulation.

10. The composition of claim 1, wherein the composition is a foam formulation capable of forming bubbles.

11. The composition of claim 1, wherein the ratio of the pigment penetration agent and the surfactant is 1:2 to 1:6.

* * * * *